US012004788B2

(12) United States Patent
Oberli et al.

(10) Patent No.: US 12,004,788 B2
(45) Date of Patent: Jun. 11, 2024

(54) BONE PLATES HAVING COMPRESSION HOLES, AND RELATED SYSTEMS AND METHODS

(71) Applicant: DePuy Synthes Products, Inc., Raynham, MA (US)

(72) Inventors: Joel Oberli, Niederdorf (CH); This Aebi, Grenchen (CH); Steffan Daniel, Solothurn (CH); Said Ghammar, Zuchwil (CH); Mirko Rocci, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 117 days.

(21) Appl. No.: 17/668,262

(22) Filed: Feb. 9, 2022

(65) Prior Publication Data

US 2022/0265328 A1    Aug. 25, 2022

Related U.S. Application Data

(60) Provisional application No. 63/147,865, filed on Feb. 10, 2021.

(51) Int. Cl.
*A61B 17/80*    (2006.01)
*A61B 17/17*    (2006.01)
(Continued)

(52) U.S. Cl.
CPC ...... *A61B 17/8014* (2013.01); *A61B 17/1728* (2013.01); *A61B 17/8057* (2013.01);
(Continued)

(58) Field of Classification Search
CPC ............... A61B 17/17; A61B 17/1728; A61B 2017/681; A61B 17/8014; A61B 17/8057; A61B 17/808; A61B 17/88; A61B 17/90
See application file for complete search history.

(56) References Cited

U.S. PATENT DOCUMENTS 4,388,921 A * 6/1983 Sutter ............... A61B 17/8047
411/537
4,599,999 A * 7/1986 Klaue ............... A61B 17/1728
606/96

(Continued)

FOREIGN PATENT DOCUMENTS

WO    2021/062102 A1    4/2021

OTHER PUBLICATIONS

U.S. Appl. No. 17/155,218, filed Jan. 22, 2021, in the name of Daniel et al.

*Primary Examiner* — Larry E Waggle, Jr.
(74) *Attorney, Agent, or Firm* — BakerHostetler

(57) ABSTRACT

A bone fixation system includes a bone plate having an outer surface, an opposed bone-facing surface, and an interior surface that defines a hole extending from the outer surface to the bone-facing surface along a central hole axis. The interior surface further defines a compression surface. The system includes a bone fixation member having a shaft extending from a head along a central fixation member axis. The head has an exterior surface that defines a threaded head portion configured for variable angle locking with a complimentary variable angle plate locking structure. The compression surface and the threaded head portion are cooperatively configured to translate the bone plate in a direction substantially perpendicular to the central hole axis when the threaded head portion contacts the compression surface when the bone fixation member axis is offset from the central hole axis at an offset parameter as the head advances within the hole.

16 Claims, 6 Drawing Sheets

(51) Int. Cl.
*A61B 17/86* (2006.01)
*A61B 17/88* (2006.01)
*A61B 17/56* (2006.01)

(52) U.S. Cl.
CPC ........ *A61B 17/808* (2013.01); *A61B 17/8605* (2013.01); *A61B 17/88* (2013.01); *A61B 2017/564* (2013.01)

(56) References Cited

U.S. PATENT DOCUMENTS

| | | | |
|---|---|---|---|
| 6,730,091 B1* | 5/2004 | Pfefferle | A61B 17/863 606/291 |
| 8,632,545 B2* | 1/2014 | Sarangapani | A61B 17/1728 606/280 |
| 9,314,284 B2 | 4/2016 | Chan et al. | |
| 9,498,267 B2* | 11/2016 | Pfeiffer | A61B 17/8014 |
| 10,772,665 B2 | 9/2020 | Bosshard et al. | |
| 2004/0097950 A1 | 5/2004 | Foley et al. | |
| 2006/0095044 A1 | 5/2006 | Grady et al. | |
| 2006/0149275 A1* | 7/2006 | Cadmus | A61B 17/151 606/88 |
| 2009/0254126 A1* | 10/2009 | Orbay | A61B 17/8004 606/301 |
| 2010/0130983 A1* | 5/2010 | Thornhill | A61B 17/1728 606/96 |
| 2013/0190829 A1 | 7/2013 | Batsch et al. | |
| 2015/0272638 A1 | 10/2015 | Langford | |
| 2019/0328430 A1 | 10/2019 | Bosshard et al. | |
| 2021/0015526 A1 | 1/2021 | Oberli et al. | |

\* cited by examiner

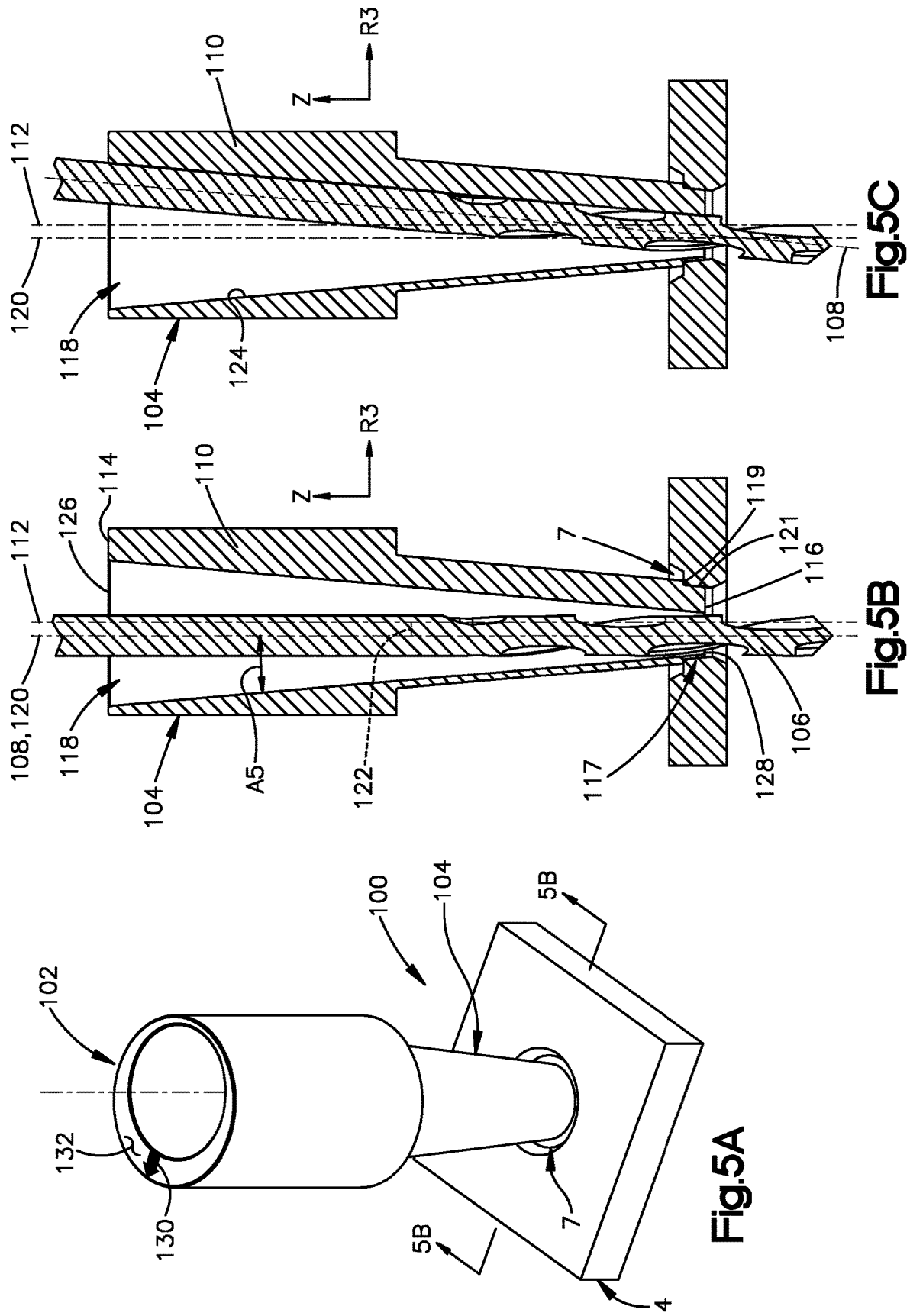

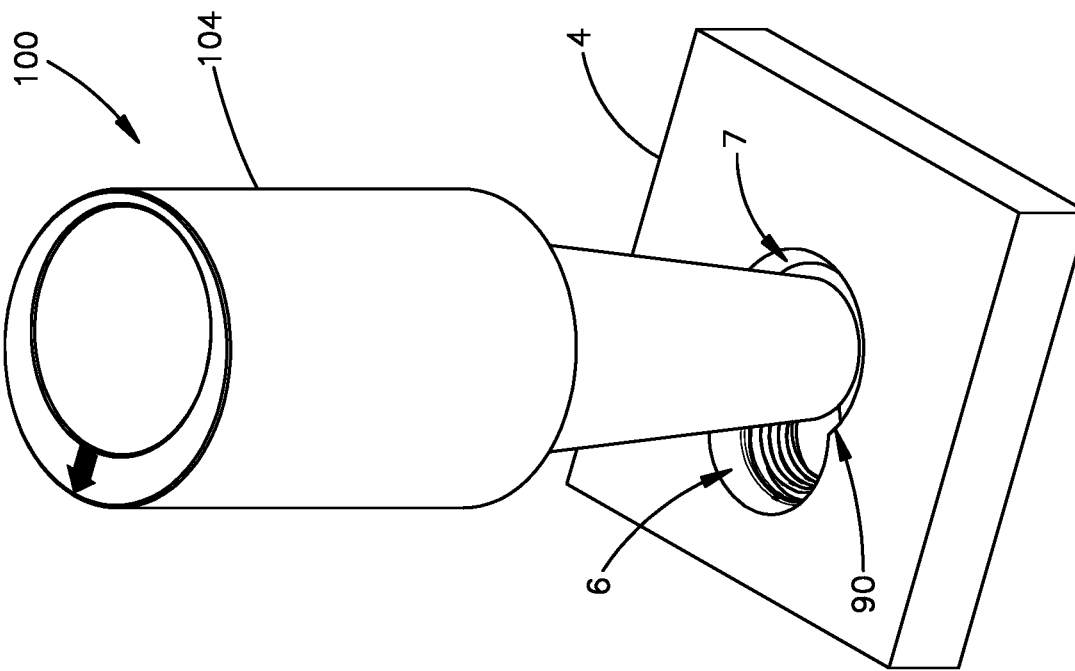
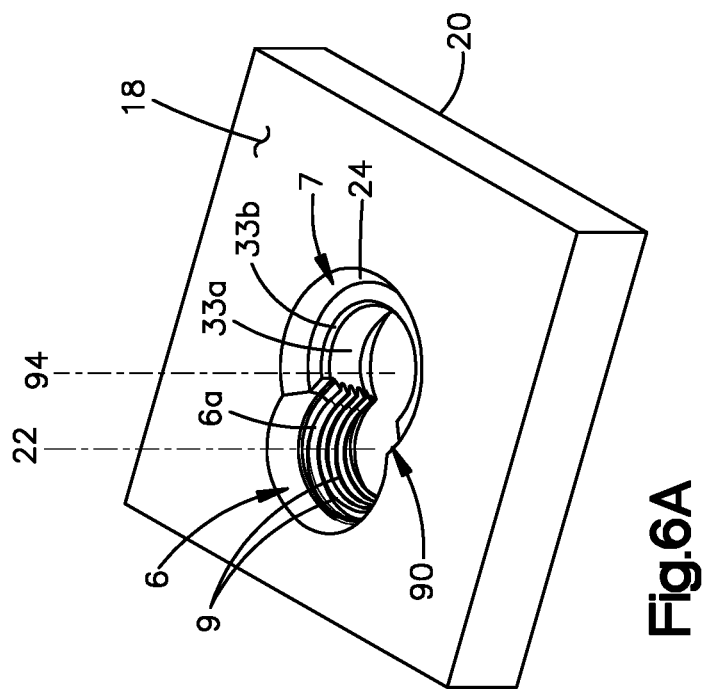
Fig.6A
Fig.6B

BONE PLATES HAVING COMPRESSION HOLES, AND RELATED SYSTEMS AND METHODS

CROSS REFERENCE TO RELATED APPLICATIONS

This application claims the benefit under 35 U.S.C. § 119(e) of U.S. Provisional Patent Application No. 63/147,865, filed Feb. 10, 2021, in the name of Oberli et al., the entire contents of which are hereby incorporated by reference.

TECHNICAL FIELD

The present invention relates to bone plates for receiving bone anchors to affix the bone plates to bone, and particularly relates to bone plates having compression holes configured to translate the bone plate along a direction substantially perpendicular to a central axis of the compression hole responsive to contact with a threaded head of a locking bone fixation member when the head is driven eccentrically within the compression hole.

BACKGROUND

Bone plate systems for the internal fixation of bone fractures are well known. Conventional bone plate systems are particularly well-suited to promote the healing of a fracture. A bone anchor, such as a bone screw, is inserted through a fixation aperture or hole in a bone plate and is threaded into bone to compress, neutralize, buttress, tension, band, and/or bridge the fracture ends together. Bone screws that are capable of locking with the bone plate can be employed to transfer loads from one fractured bone part, over a plate, and onto another fractured bone part without drawing the bone against the plate, and to avoid loosening or backing out the bone screws with respect to the plate (which can lead to poor alignment and poor clinical results). One known embodiment of such a screw employs a screw head with external threads for engaging with a corresponding thread on the inner surface of a fixation hole, which are hereinafter referred to as "locking holes", to lock the screw to the plate. These screws, which are hereinafter referred to as "locking screws", can include standard-type locking screws that are configured to lock within a fixation hole substantially only at a "nominal" orientation whereby the central screw axis is substantially aligned with the central hole axis, as well as "variable-angle" (VA) locking screws that are configured to lock within a fixation hole at either a nominal orientation or an "angulated" orientation whereby the central screw axis is oriented at an acute angle with respect to the respective central hole axis.

Bone plate systems can also be adapted to provide anatomical reduction between fractured bone parts. The bone plates of such systems include one or more holes having ramp geometries that engage a smooth exterior surface of a screw head of a "compression screw" in a manner causing dynamic compression, meaning that the bone plate translates with respect to the compression screw and underlying bone along a direction generally perpendicular to the screw axis of the compression screw. Such holes are hereinafter referred to as "compression holes". Bone plates can include both locking holes and compression holes. Additionally or alternatively, bone plates can include combination holes or "combi-holes" that include a locking hole and a compression hole that intersect one another, such that the locking hole and the compression hole overlap one another and are open to each other. Combi-holes are commonly used selectively for either locking the plate to underlying bone (by inserting a locking screw within the locking hole of the combi-hole) or translating the plate relative to the underlying bone (by inserting a compression screw within the compression hole of the combi-hole).

SUMMARY

According to an embodiment of the present disclosure, a system for bone fixation includes a bone plate having an outer surface, a bone-facing surface opposite the outer surface, and an interior surface that defines a hole that extends from the outer surface to the bone-facing surface along a central hole axis. The interior surface further defines a compression surface. The system includes a bone fixation member having a head and a shaft that extends from the head along a central fixation member axis. The head has an exterior surface that defines a threaded head portion that is configured for variable angle locking with a complimentary variable angle plate locking structure. The compression surface and the threaded head portion are cooperatively configured to translate the bone plate in a translation direction that is substantially perpendicular to the central hole axis responsive to the threaded head portion contacting the compression surface when the bone fixation member axis is offset from the central hole axis at an offset parameter as the head advances within the hole toward underlying bone.

According to another embodiment of the present disclosure, a system for bone fixation includes a bone plate having an outer surface, a bone-facing surface opposite the outer surface, and an interior surface that defines a hole that extends from the outer surface to the bone-facing surface along a central hole axis. The interior surface further defines a compression surface that is configured to cause translation of the bone plate in a translation direction upon contact with a threaded head of a bone fixation member when the head advances within the hole toward underlying bone along a bone fixation member axis that is offset from the central hole axis at an offset parameter. The translation direction is substantially perpendicular to the central hole axis. The system includes a guide sleeve that defines a central sleeve axis, a proximal end, a distal end opposite the proximal end, and a bore surface that defines a guide channel extending from the proximal end to the distal end along a central channel axis that is offset from the central sleeve axis along an offset axis oriented along a second direction that is perpendicular to the central sleeve axis. The distal end of the guide sleeve defines a mounting formation configured to seat against the interior surface within the hole such that the central sleeve axis is substantially parallel to the central hole axis. The bore surface tapers toward the central channel axis and toward the distal end such that the bore surface is configured to provide guided polyaxial insertion of a drill through the hole toward the underlying bone along a selective trajectory axis that defines the offset parameter.

According to an additional embodiment of the present disclosure, a method of bone fixation includes inserting a shaft of a bone fixation member through a hole in a bone plate along an insertion axis and into underlying bone. The bone plate comprises an outer surface, a bone-facing surface opposite the outer surface, and an interior surface that defines the hole. The hole extends along a central hole axis, and the insertion axis is offset from the central hole axis at an offset parameter. The method includes contacting a threaded portion of an exterior surface of a head of the bone fixation member against a compression surface within the hole, wherein the compression surface is defined by the interior surface. The method also includes driving the bone fixation member, during the contacting step, toward the underlying bone along the insertion axis in a manner translating the bone plate in a translation direction that is substantially perpendicular to the central hole axis.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 5A is a perspective view of a bone plating system that includes a drill guide inserted within the compression hole, according to an embodiment of the present disclosure;

FIG. 5B is a sectional side view of the drill guide of FIG. 5A taken along section 5B-5B, showing a drill bit inserted therethrough along a nominal insertion axis;

FIG. 5C is a sectional side view of the drill guide showing the drill bit inserted therethrough along an angulated insertion axis;

FIG. 6A is a perspective view of the compression hole of FIG. 1A incorporated into a combination hole;

FIG. 6B is a perspective view of a bone plating system that includes a drill guide inserted within the compression hole portion of the combi-hole, according to an embodiment of the present disclosure.

DETAILED DESCRIPTION OF ILLUSTRATIVE EMBODIMENTS

Figure 1A:
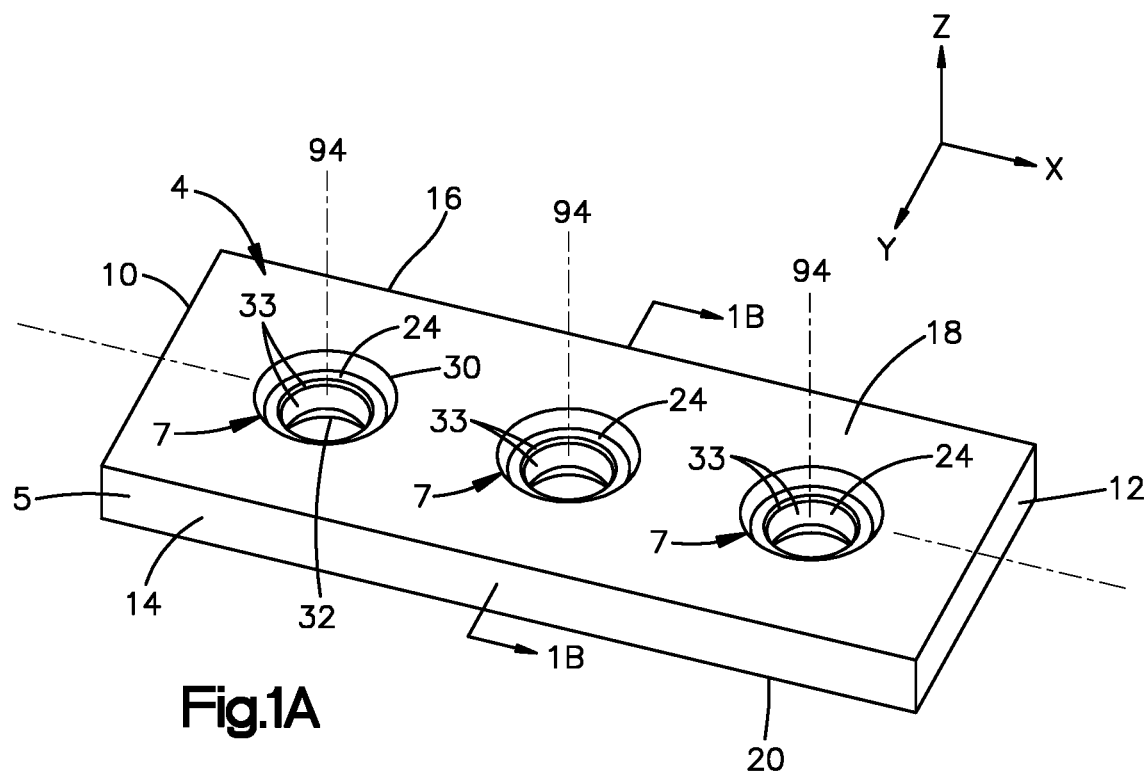
FIG. 1A is a perspective view of a bone plate having compression holes extending therethrough, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately", "about", and "substantially", as used herein with respect to dimensions, angles, and other geometries, takes into account manufacturing tolerances. Further, the terms "approximately", "about", and "substantially" can include 10% greater than or less than the stated dimension or angle. Further, the terms "approximately", "about", and "substantially" can equally apply to the specific value stated.

As used herein, the term "dynamic compression" refers to an act of engaging a bone anchor against a bone plate in a manner causing the bone plate to translate relative to the bone anchor and underlying patient anatomy (e.g., underlying bone) along a direction that is substantially perpendicular to a central axis of a hole in the bone plate through which the bone anchor is inserted into underlying bone. Dynamic compression is particularly useful for moving fractured portions of bone relative to one another, such as for anatomical reduction to treat bone fractures. Typically, dynamic compression is achieved by contacting a smooth, generally spherical head of a compression fixation member, such as a compression screw (also referred to as a "cortex screw") against a ramp-like surface of a hole, such as a "compression hole", defined in the bone plate. Such compression holes, along with the heads of such associated compression fixation members, tend to be larger than their counterparts designed for locking engagement (e.g., locking holes and locking bone fixation members).

The embodiments disclosed herein pertain to compression holes in a bone plate, particularly compression holes having geometries that are configured to provide dynamic compression when contacted with a threaded head of a locking bone fixation member, such as a VA locking bone fixation member (e.g., a VA locking screw). The compression holes of the present disclosure provide significant advantages over prior art compression holes. For example, the compression hole geometries described herein allow for a smaller compression hole relative to prior art compression holes. These smaller holes can allow the associated bone plates to include a greater number of such holes therein, and thus also provide a greater number of associated bone fixation members to affix the bone plate to underlying bone. The compression holes described below can also allow a single locking bone fixation member to perform both dynamic compression and locking functions with the bone plate. Thus, the single locking bone fixation member of the present disclosure can also be referred to as "multi-use" single locking bone fixation member. The embodiments described herein also allow a VA bone fixation member to cause dynamic compression using an angulated insertion trajectory into the underlying bone. Additional benefits include that the smaller head of the locking bone fixation member can result in a lower head prominence from an outer surface of the bone plate when the head is fully seated in the compression hole.

The inventors have discovered, surprisingly and unexpectedly, that compression holes having certain hole geometries can be alternatively used with the threaded heads of locking bone fixation members to achieve dynamic compression, even when the contact that drives the translation occurs between the compression surface and a threaded head of a locking bone fixation member. In this manner, the multi-use single locking bone fixation member of the present disclosure can provide selective dynamic compression and/or locking engagement without the need for a dedicated compression bone fixation member. Additionally, the higher hole density, combined with the option to use each hole for dynamic compression and/or for locking, provides enhanced patient-specific fracture fixation treatment, which provides further advantages in that such treatments can be less invasive and require a shorter healing and recovery period.

Figure 1B:
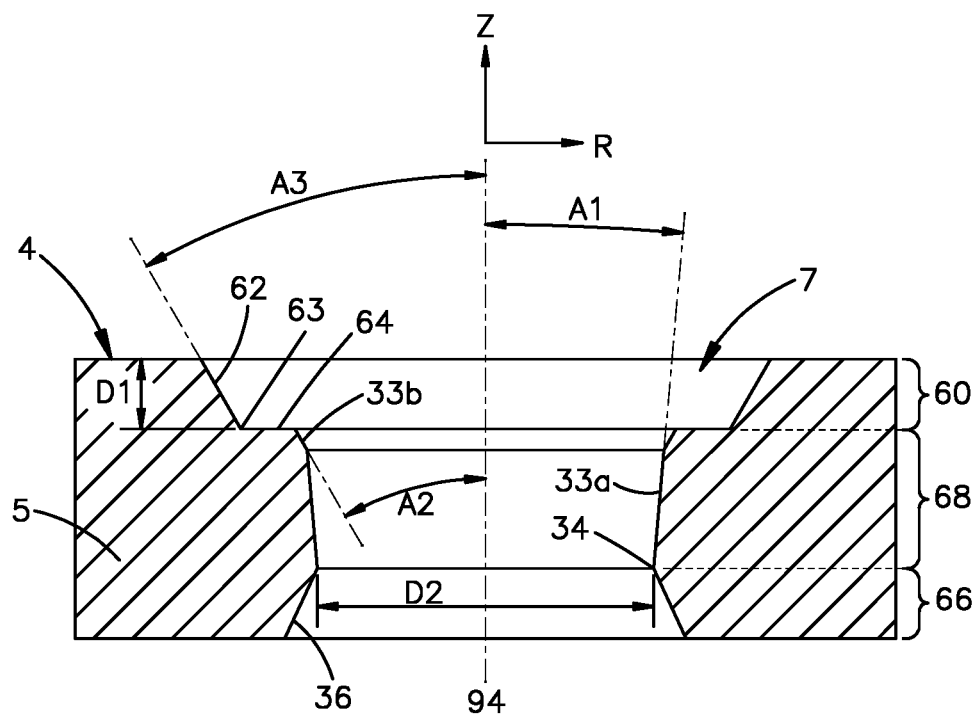
FIG. 1B is a sectional side view of a compression hole of the bone plate, taken along section line 1B-1B of FIG. 1A.

Referring to FIGS. 1A and 1B, a bone plate 4 according to an embodiment of the present disclosure has a plate body 5 that defines therein one or more compression holes 7. The plate body 5 defines interior surfaces 24 that respectively define the holes 7. The compression holes 7 are configured to receive a locking bone anchor 8 for affixing the bone plate 4 to underlying bone. Within each compression hole 7, the interior surface 24 further defines one or more compression surfaces 33, which can also be referred to as ramp surfaces 33 or "ramps" 33. Each compression surface 33 is configured to engage a threaded head 27 of the locking bone anchor 8 in a manner causing dynamic compression, as described in more detail below.

The bone plate 4 can be a bridge plate, although other bone plate types and configurations are within the scope of the present disclosure. The plate body 5 can define a first end 10 and a second end 12 spaced from each other along the longitudinal direction X. The plate body 5 can also define a first lateral side 14 and a second lateral side 16 spaced from each other along a lateral direction Y that is substantially perpendicular to the longitudinal direction X. The bone plate 4 can also define an upper plate surface 18 (also referred to herein as an "outer surface" 18) configured to face away from the bone and an opposed lower plate surface 20 (also referred to herein as a "bone-facing surface") configured to face the bone. The interior surface 24 of each compression hole 7 extends from an upper perimeter 30 at an interface with the upper plate surface 18 to a lower perimeter 32 at an interface with the lower plate surface 20. The upper and lower plate surfaces 18, 20 are spaced from each other along a vertical direction Z substantially perpendicular to each of the longitudinal direction X and the lateral direction Y. It is to be appreciated that, as used herein, the terms "longitudinal", "longitudinally", and derivatives thereof refer to the longitudinal direction X; the terms "lateral", "laterally", and derivatives thereof refer to the lateral direction Y; and the terms "vertical", "vertically", and derivatives thereof refer to the vertical direction Z. It should also be appreciated that a plane that contains the longitudinal and laterals directions X, Y can be referred to herein as a "horizontal" plane X-Y.

The compression holes 7 can each extend from the upper plate surface 18 to the lower plate surface 20 along a central hole axis 94. The central hole axis 94 is oriented along an axial hole direction. As used herein, the term "axial direction" (e.g., "axial hole direction" and "axial screw direction") is defined as the direction along which the respective axis extends. Furthermore, the directional terms "axial", "axially", and derivatives thereof refer to the respective axial direction. Thus, as used herein, the directional term "axially upward" and derivatives thereof refers to the axial hole direction from the lower plate surface 20 toward the upper plate surface 18. Conversely, the term "axially downward" and derivatives thereof refers to the axial hole direction from the upper plate surface 18 toward the lower plate surface 20. Thus, "axially upward" and "axially downward" are each mono-directional components of the "axial direction", which is bi-directional. In the embodiments depicted in the Figures, the axial hole direction (and thus also the central hole axis 94) is oriented along the vertical direction Z. Accordingly, the axial hole direction is also denoted by "Z" throughout this disclosure. It should be appreciated, however, that the scope of the present disclosure covers embodiments in which the axial hole direction (and thus also the central hole axis 94) is offset from the vertical direction Z at an oblique angle. It should also be appreciated that when the terms "axially upper", "axially lower," and the like are used with reference to a locking bone anchor 8, such terms refer to a central axis 52 of the anchor, particularly as the anchor would be oriented within the hole 7 (see FIGS. 3A-4B).

The interior surface 24 of the compression hole 7 defines at least one compression surface 33, such as a first or "primary" compression surface 33a extending between the upper and lower plate surfaces 18, 20. The first compression surface 33a tapers inwardly toward the central hole axis 94 (and toward the lower plate surface 20) at a ramp angle A1. As shown in FIG. 1B, the first compression surface 33a can taper along a linear profile in a reference plane that extends along the central hole axis 94 (which can thus be referred to as an "axial reference plane"). Ramp angle A1 can be in a range from about 0.5 degrees to about 15 degrees, and more particularly in a range from about 2 degrees to about 7.5 degrees, and more particularly in a range of about 4 degrees to about 6 degrees. The first compression surface 33a can extend an entire revolution about the central hole axis 94, although in other embodiments the first compression surface 33a can extend less than an entire revolution about the central hole axis 94. As shown, the first compression surface 33a can be smooth and can also be devoid of protrusions and/or recesses. In the illustrated embodiment, the first compression surface 33a has a downward-tapering frustoconical shape, particularly that of a right circular cone having a central cone axis coincident with the central hole axis 94. It should be appreciated that the first compression surface 33a can have other geometries. For example, one or more portions of the first compression surface 33a can taper along an arcuate profile in the axial reference plane.

The interior surface 24 can also define one or more additional compression surfaces, such as a second compression surface 33b, which can extend axially between the upper plate surface 18 and the first compression surface 33a. The second compression surface 33b can be referred to as a "lead-in" compression surface 33b or chamfer, and can be contiguous with the first compression surface 33a. The second compression surface 33b tapers inwardly toward the central hole axis 94 (and toward the lower plate surface 20), such as along a linear profile in the reference plane. The second compression surface 33b defines a second ramp angle A2, which is preferably shallower than ramp angle A1. Ramp angle A2 can be in a range from about 5 degrees to about 85 degrees, and more particularly in a range from about 15 degrees to about 45 degrees, and more particularly in a range of about 25 degrees to about 35 degrees. The second compression surface 33b can extend an entire revolution about the central hole axis 94, although in other embodiments the first second surface 33b can extend less than an entire revolution about the central hole axis 94. The second compression surface 33b can be smooth and can also be devoid of protrusions and/or recesses. In the illustrated embodiment, the second compression surface 33b has a downward-tapering frusto-conical shape, particularly that of a right circular cone having a central cone axis coincident with the central hole axis 94. It should be appreciated, however, that the second compression surface 33b can have other geometries. For example, one or more portions of the second compression surface 33b can taper along an arcuate profile in the axial reference plane.

The compression hole 7 preferably includes an entry portion 60, such as a countersink, adjacent the upper perimeter 30. For example, within the entry portion 60, the interior surface 24 can include a countersink surface 62 that extends from the upper perimeter 30 toward the compression surfaces 33a-b. The countersink surface 62 tapers inwardly toward the central hole axis 94 at a ramp angle A3. The countersink surface 62 can taper linearly, and can extend a full revolution about the central hole axis 94 in a manner defining a downward-tapering frusto-conical shape, although the countersink surface 62 can have other geometries. The entry portion 60 can also include a landing surface 64 (also referred to herein as a "landing" 64) positioned between the countersink surface 62 and the compression surfaces 33a-b. The landing 64 can extend from a lower perimeter 63 of the countersink surface 62 toward the central hole axis 94. The landing 64 can be planar and can be oriented orthogonally with respect to the central hole axis 94. Accordingly, the landing 64 can extend inwardly toward the central hole axis 94 along a radial direction R that is substantially perpendicular to the central hole axis 94. It should be appreciated, however, that other landing 64 geometries are within the scope of the present disclosure. The landing 64 is recessed from the upper plate surface 18 at a recess distance D1 measured along the vertical direction Z. The entry portion 60 is preferably configured to reduce or eliminate any distance by which the head of the locking bone anchor extends outwardly from the upper plate surface 18 when the head is fully seated within the hole 7.

The compression hole 7 also preferably includes a lower relief portion 66 adjacent the lower perimeter 32. For example, within the lower relief portion 66, the interior surface 24 can include an undercut surface 36 (also referred to herein as a "relief surface") that extends axially upward from the lower perimeter 32 toward the first compression surface 33a. As shown, the undercut surface 36 can extend to, and be contiguous with, a lower perimeter 34 of the first compression surface 33a. The lower perimeter 34 of the first compression surface 33a preferably defines a minimum inner diameter D2 of the hole 7, measured along the radial direction R. The undercut surface 36 can taper linearly, and can extend a full revolution about the central hole axis 94 in a manner defining an upward-tapering frusto-conical shape, although the undercut surface 36 can have other geometries. The hole 7 is configured such that minimum inner diameter D2 is greater than a major diameter of a threaded shaft of a locking screw for insertion therethrough. The lower relief portion 66 is configured to provide clearance along the radial direction R for threads of the threaded shaft of the locking screw 8 during eccentric and/or angulated screw insertion through the hole 7. The hole 7 can be characterized as defining a plurality of distinct axial regions or portions along the central hole axis 94, such as the entry portion 60, the lower relief portion 66, and a compression portion 68 (along which the compression surfaces 33a-b extend) located axially between the entry and lower relief portions 60, 66.

Figure 2:
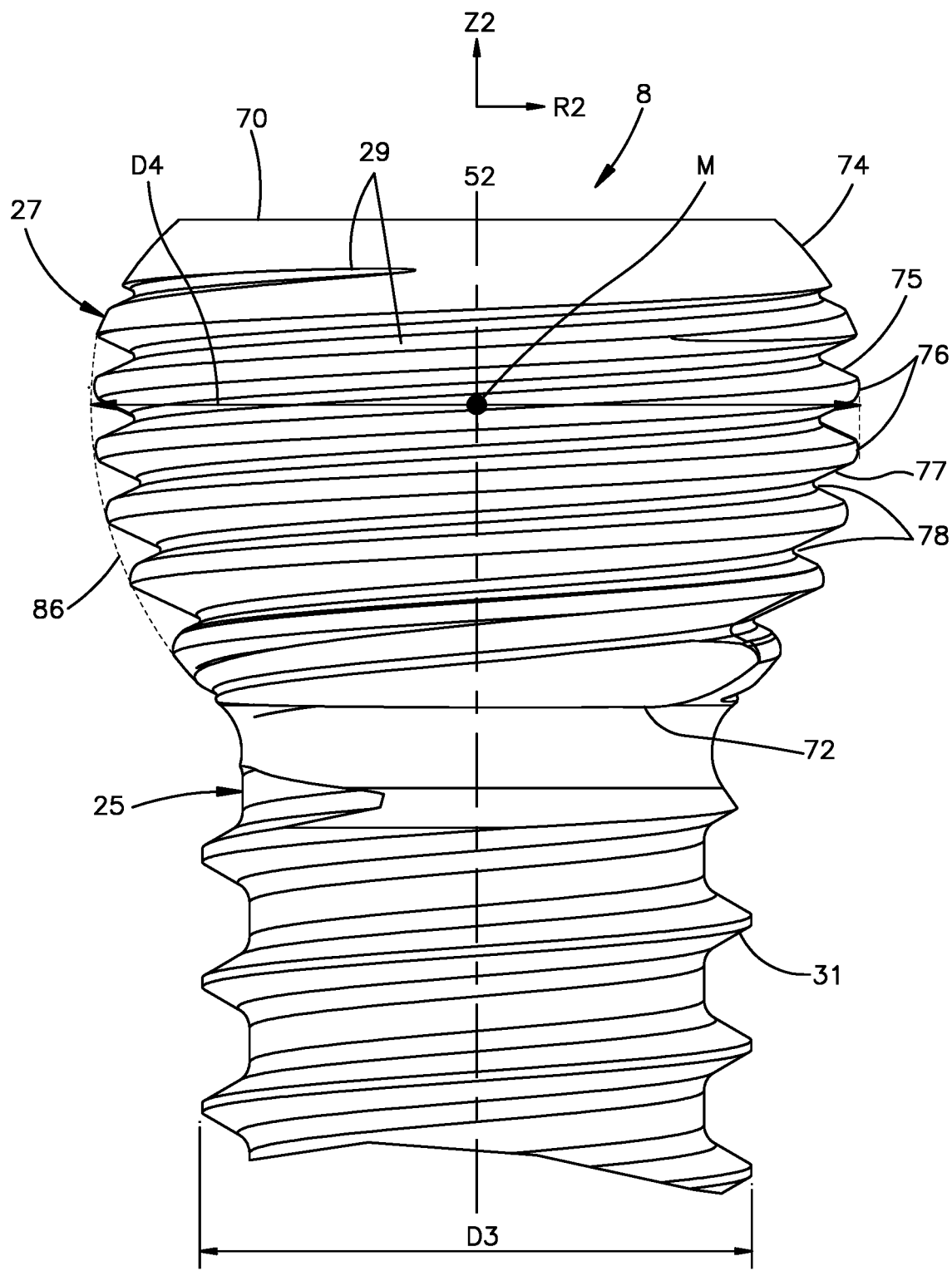
FIG. 2 is a front view of a prior art locking screw configured for use with the compression holes shown in FIGS. 1A-1B.

Referring now to FIG. 2, depicted is a proximal portion of an example prior art VA locking screw 8 for use with the compression holes 7 of the present disclosure. The VA locking screw 8 has a head 27 and a shaft 25 that extends from the head 27 along an axial screw direction Z2 oriented along the central screw axis 52. The shaft 25 includes threads 31 for purchase within bone. The shaft threads 31 define a major thread diameter D3 measured along a radial head direction R2 perpendicular to the axial screw direction Z2.

The head 27 defines a proximal end 70 and a distal end 72 spaced from each other along the axial screw direction Z2. The head 27 also defines an exterior surface 74 that extends from the proximal end 70 to the distal end 72 and defines external screw head threads 29. The external screw head threads 29 extend substantially from the proximal end 70 to substantially the distal end 72 of the head 27 along one or more thread paths, which can be helical. The external screw head threads 29 define crests 76 spaced radially outwardly from roots 78 with respect to the central screw axis 52. The screw head threads 29 also define upper flanks 75 and lower flanks 77 that extend from the crests 76 to respective axially upper and lower roots 78.

In an axial reference plane that extends along the central screw axis 52, the external screw head threads 29 define a crest profile axis 86 that intersects the crests 76. As shown, the crest profile axis 86 can define an arcuate, convex shape, which is advantageous for angulated locking when the head 27 is inserted within a locking hole having complimentary interior plate threads 9. In additional embodiments, the crest profile axis 86 can be generally spherical. It should be appreciated, however, that other crest profile axis 86 geometries are within the scope of the present disclosure, including those associated with nominal-type locking screws (i.e., those types configured for only nominal locking with a locking hole). The screw head 27 defines a maximum head diameter D4, which can be measured between the crest profile axes 86 on opposite sides of the head 27 along the radial head direction R2. The screw head 27 can also define a reference midpoint M at the location along the central screw axis 52 that coincides with the maximum head diameter D4. The crest profile axes of the heads of VA locking screws and nominal-type locking screws are described more fully in U.S. Pat. No. 9,314,284, issued Apr. 19, 2016, in the name of Chan et al. ("the '284 Reference"); U.S. Pat. No. 10,772,665, issued Sep. 15, 2020, in the name of Bosshard, et al. ("the '665 Reference"); US Patent Publication No. 2019/0328430 A1, published Oct. 31, 2019, in the name of Bosshard, et al. ("the '430 Reference"); and U.S. application Ser. No. 17/062,708, filed Oct. 5, 2020, in the name of Oberli et al. ("the '708 Reference"), the disclosures of each of which are hereby incorporated by reference as if set forth in their entireties herein.

The compression surfaces 33a-b of the hole 7 are configured to engage the threaded head 27, particularly the threads 29 thereof, particularly the crests 76, in a manner causing dynamic compression when the screw 8 is inserted along a central screw axis 52 that is offset from the central hole axis 94 according to at least one offset parameter, such as an eccentric screw axis 52 and/or an angulated screw axis 52. Methods of using the compression hole 7 in a bone plating operation for dynamic compression will now be described, according to example techniques of inserting a locking screw 8 according to such offset parameters.

Figure 3A:
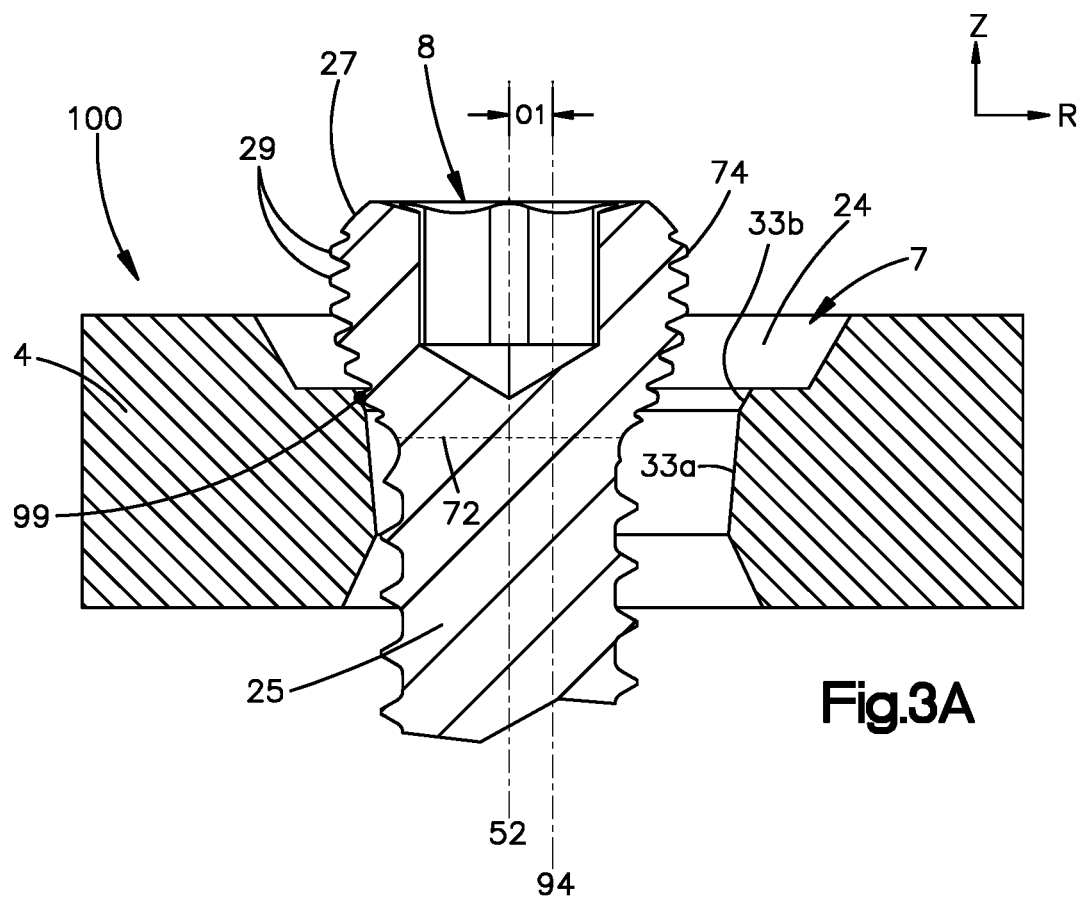
FIG. 3A is the sectional side view of the compression hole illustrated in FIG. 1B showing a locking screw inserted eccentrically therein at a first contact position, according to an embodiment of the present disclosure.
Figure 3B:
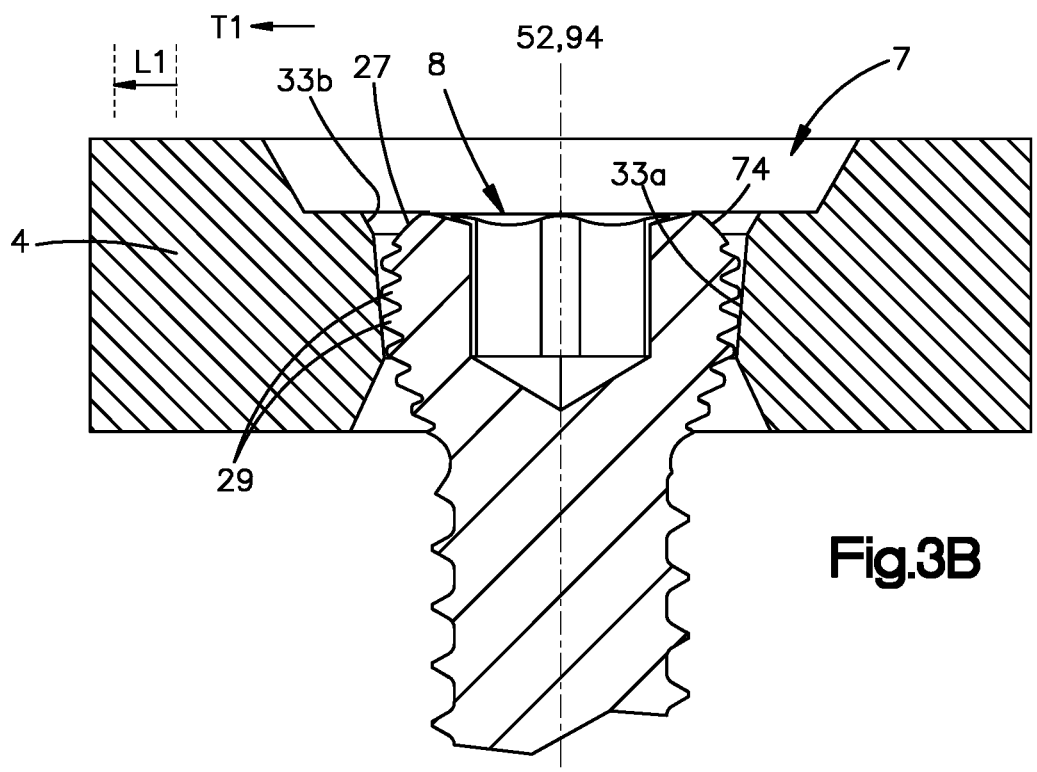
FIG. 3B is the sectional side view of the compression hole illustrated in FIG. 1B showing the locking screw inserted therein at a fully seated position.

Referring now to FIGS. 3A and 3B, an example method of using the compression hole 7 for dynamic compression responsive to eccentric, nominal screw insertion will be described. During the bone plating operation, a physician can insert the shaft 25 of the locking screw 8 through the hole 7 along an insertion axis, which can be substantially parallel with the central hole axis 94 (i.e., a nominal insertion angle). The locking screw 8 and the bone plate 4 can characterized as being constituent components of a bone plating system 100. In the embodiments illustrated herein, the insertion axis is coaxial with the central screw axis 52; accordingly, the central screw axis 52 can be used herein interchangeably with the insertion axis. During screw insertion, the physician can drive the shaft 25 into underlying bone, such as a bone segment 100, along the nominal insertion axis 52. In this example, the physician can cause the insertion axis 52 to be eccentric, meaning that the insertion axis 52 is offset from the central hole axis 94 by an offset distance O1 measured in a direction perpendicular to the central hole axis 94, such as the radial direction R. Thus, in the present example, the offset distance O1 is the offset parameter by which the insertion axis 52 is offset from the central hole axis 94.

As shown in FIG. 3A, the physician can drive the shaft 25 through the hole 7 along the eccentric insertion axis 52 in a manner causing the exterior surface 74 of the head 27, such as a threaded portion thereof, to engage the interior surface 24 of the hole 7 at a first position of the screw head 27 with respect to the interior surface 24. At the first position, the exterior surface 74 of the screw head 27 contacts the interior surface 24 within the hole 7 at a first initial contact location 99, which can occur along the second compression surface 33b of the hole 7 and at a crest 76 of the head threads 29, such as a crest 76 near the distal end 72 of the head 27 It should be appreciated that a maximum of the offset distance O1 can be determined by a variety of factors, such as the minimum inner diameter D2 of the hole 7 and the major thread diameter D3 of the threaded shaft 25, for example.

As shown in FIG. 3B, after the exterior surface 74 of the head 27 contacts the interior surface 24 at the first initial contact location 99 (FIG. 3A), the physician can further drive the locking screw 8 axially downward along the insertion axis 52, causing the exterior surface 74 of the head 27 to travel or ride along the interior surface 24, such as along the second compression surface 33b and along the first compression surface 33a, to a second position of the screw head 27 relative to the interior surface 24, (FIG. 3B) which can be a fully seated position of the screw head 27 within the hole 7. The interfacing geometries of the interior surface 24 of the hole 7, particularly along the compression surfaces 33a-b, and the exterior surface 74 of the head 27, particularly the crests 76 (i.e., along the crest profile axis 86 (FIG. 2)) causes the plate 4 and the underlying bone segment 100 to translate in a translation direction T1 as the exterior surface 74 rides along the interior surface 24, as the screw head 27 advances axially downward along the insertion axis 52. In this manner, the bone segment 100 can translate in the translation direction T1 in a manner reducing a gap G between the bone segment 100 and an adjacent bone segment 102.

In the present embodiment, the complimentary geometries of the screw head 27 and the compression surfaces 33a-b, particularly the first compression surface 33a, are configured such that the screw axis 52 will be substantially co-extensive with the central hole axis 94 when the screw head 27 is fully seated within the hole 7 at the conclusion of the plate translation. In such embodiments, the offset distance O1 effectively defines a translation distance L1 of the plate 4 (i.e., the distance L1 along which the plate 4 translates) along the radial direction R provided by the eccentric, nominal screw insertion. It should be appreciated that the symmetry of the interior surface 24, particularly the compression surfaces 33a-b thereof, about the central hole axis 94 allows the translation direction T1 to be selected at virtually any direction extending perpendicularly away from the central hole axis 94 (i.e., from 0 degrees to 360 degrees about the central hole axis 94). Such directions can be referred to as "clocking directions." In the present embodiment, pre-selection of the translation direction T1 can be achieved by selecting a nominal insertion axis 52 at the desired clocking direction; and pre-selection of the translation distance L1 can be achieved by selecting the offset distance O1.

Figure 4A:
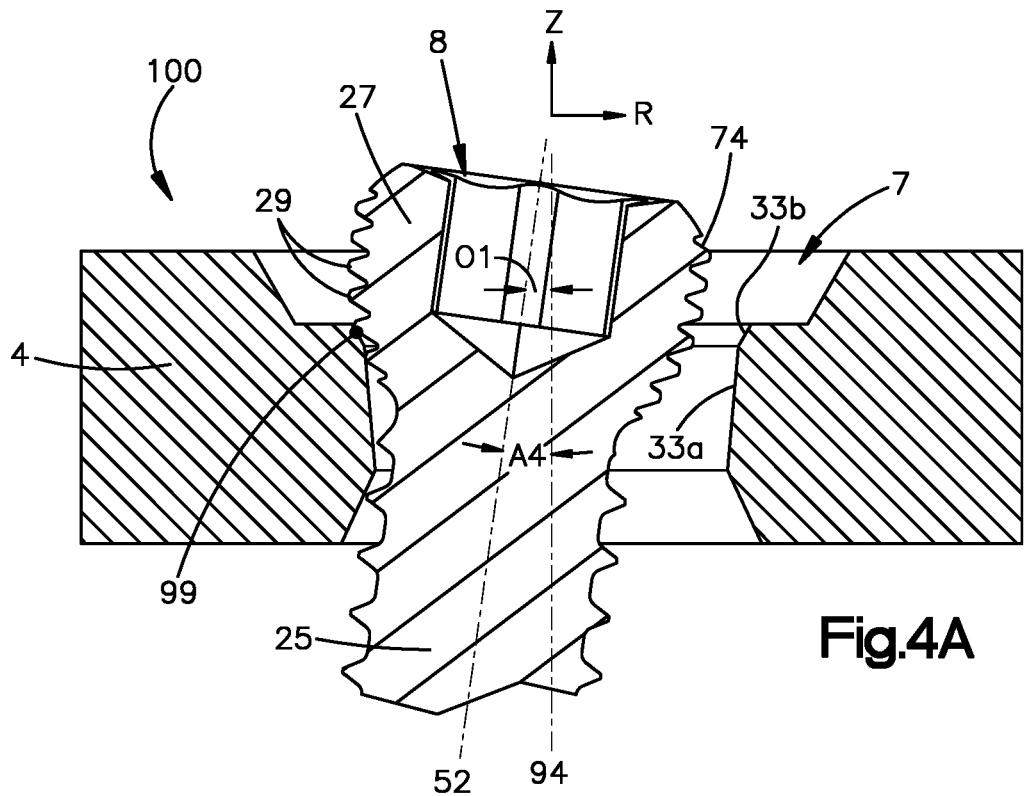
FIG. 4A is the sectional side view of the compression hole illustrated in FIG. 1B showing a locking screw inserted eccentrically and at angulation therein at a first contact position, according to an embodiment of the present disclosure.
Figure 4B:
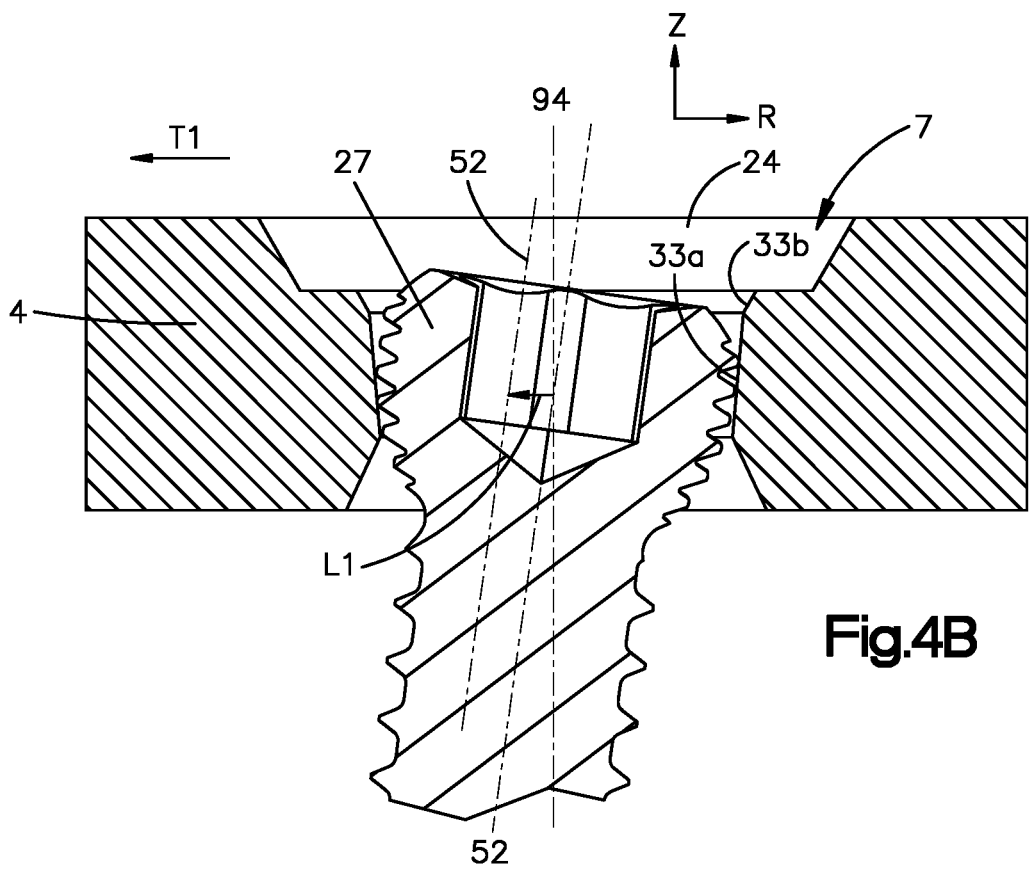
FIG. 4B is the sectional side view of the compression hole illustrated in FIG. 1B showing the angulated locking screw inserted therein at a fully seated position.

Referring now to FIGS. 4A and 4B, an example method of using the compression hole 7 for dynamic compression responsive to eccentric, angulated screw insertion will be described. The physician can insert the shaft 25 of the locking screw 8 through the hole 7 along an insertion axis 52 that is angulated relative to the central hole axis 94 at angulation A4, which can be in a range of about 0 degrees to about 10 degrees. The physician can also cause the insertion axis 52 to be offset from the central hole axis 94 by an offset distance O1 in the radial direction R. Thus, in the present example, both the offset distance O1 and the angulation A4 are offset parameters by which the insertion axis 52 is offset from the central hole axis 94. It should be appreciated that when the insertion axis 52 is both eccentric and angulated, the offset distance O1 can be measured at the reference midpoint M of the head 27 (see FIG. 2).

As shown in FIG. 4A, the physician can drive the shaft 25 through the hole 7 along the eccentric, angulated insertion axis 52 in a manner causing the exterior surface 74 of the head 27 to engage the interior surface 24 of the hole 7 at a first position of the screw head 27 with respect to the interior surface 24. At the first position, the exterior surface 74 of the screw head 27 contacts the interior surface 24 within the hole 7 at a first initial contact location 99, which again can occur along the second compression surface 33b of the hole 7 and at a crest 76 of the head threads 29, such as a crest 76 near the distal end 72 of the head 27. During an eccentric and angulated screw insertion, it should be appreciated that a maximum of the offset distance O1 can be determined by a variety of factors, such as the angulation A4, the minimum inner diameter D2 of the hole 7, and the major thread diameter D3 of the threaded shaft 25, for example.

As shown in FIG. 4B, after the exterior surface 74 of the head 27 contacts the interior surface 24 at the first initial contact location 99 (FIG. 4A), the physician can further drive the locking screw 8 along the insertion axis 52, causing the exterior surface 74 of the head 27 to travel or ride along the interior surface 24, such as along the second compression surface 33b and along the first compression surface 33a, to a second position of the screw head 27 relative to the interior surface 24, (FIG. 4B) which can be a fully seated position of the screw head 27 within the hole 7. As above, the interfacing geometries of the compression surfaces 33a-b of the hole 7 and the crests 76 of the screw head 27 causes the plate 4 and the underlying bone segment 100 to translate in a translation direction T1 as the screw head 27 advances along the insertion axis 52. In this manner, the bone segment 100 can translate in the translation direction T1 in a manner reducing a gap G between the bone segment 100 and an adjacent bone segment 102.

In the present example of eccentric, angulated screw insertion, the complimentary geometries of the screw head 27 and the compression surfaces 33a-b, particularly the first compression surface 33a, are configured such that the screw axis 52 will at least substantially intersect the central hole axis 94 when the screw head 27 is fully seated within the hole 7, as shown. In such embodiments, the translation distance L1 of the plate 4 can be measured as the distance, along the radial direction R, between the insertion axis 52 at the first position and the insertion axis 52 at the second position. provided by the eccentric, nominal screw insertion. As with the eccentric, nominal screw insertion example above, it should be appreciated that the symmetry of the interior surface 24, particularly the compression surfaces 33a-b thereof, about the central hole axis 94 allows the physician to select the translation direction T1 at virtually any clocking direction (i.e., from 0 degrees to 360 degrees about the central hole axis 94) for eccentric, angulated screw insertion.

It should be appreciated that the complimentary geometries of the first compression surface 33a (particularly ramp angle A1 and the minimum inner diameter D2) and the head 27 (particularly the maximum head diameter D4) are preferably configured to prevent the head 27 from by advancing entirely through the compression portion 68 of the hole 7, during both nominal and angulated screw insertions. Additionally, the complimentary configurations of the screw head 27 and the compression surfaces 33a-b, particularly the first compression surface 33a, can be adapted to cause the screw head 27 to substantially affix to the plate body 5 when the head 27 is fully seated. For example, the plate body 5 along the first compression surface 33a and/or the screw head threads 29 can be configured so that torqueing the screw head 27 during axial advancement generates a sufficient radial compression force such that friction at the interface (between the first compression surface 33a and screw head threads 29) substantially affixes the head 27 to the plate body 5 when the head 27 is fully seated, including at nominal and angulated screw insertions. Additionally, the plate body 5 along the first compression surface 33a and/or the screw head threads 29 can be configured so that the radial compression load is sufficient to deform the compression surface 33a and/or the screw head threads 29, thereby increasing the affixation of the screw head 27 to the plate body 5. In further embodiments, the plate body 5 can define one or more threads along the first compression surface 33a configured to engage the screw head threads 29.

Referring now to FIGS. 5A-5C, the bone plating system 100 can also include a guide assembly 102 for providing selective guiding of the screw insertion axis. The guide assembly 102 can include a drill guide 104 configured to seat against the interior surface 24 of the hole 7 and provide guided insertion of a drill bit 106 through the hole 7 and into the underlying bone. In this manner, the guide assembly 102 can be used to pre-drill a hole within the underlying bone along a drill insertion axis 108 that can pre-define the screw insertion axis 52.

The drill guide 104 can be a guide sleeve having a sleeve body 110 that defines a central sleeve axis 112, a proximal end 114, and a distal end 116 spaced from the proximal end 114 along a sleeve axial direction oriented along the central sleeve axis 112. The sleeve body 110 also defines a guide channel 118, which can extend from the proximal end 114 to the distal end 116 along a central channel axis 120. The distal end 116 preferably defines a mounting formation 117 configured to seat against the interior surface 24 of the hole 7, preferably in a secure fashion so that the central sleeve axis 112 is substantially parallel to the central hole axis 94. For example, the mounting formation 117 can include a shoulder 119 configured to abut the landing 64, and can further include an insertion portion 121 configured to extend within the compression portion 68 of the hole 7. Preferably, the insertion portion 121 defines an outer surface 123 having a geometry complimentary with that of the first compression surface 33a and configured to seat snugly against the first compression surface 33a.

As shown, the central channel axis 120 can be offset from the central sleeve axis 112 along a direction R3 that is perpendicular to the central sleeve axis 112. In this manner, the guide channel 118 can be characterized as being a "de-centric" guide channel. The guide channel 118 can also define an offset axis 122 that intersects the central sleeve axis 112 and the central channel axis 120, and is thus oriented along direction R3. The guide channel 118 can be defined by a bore surface 124 defined by the sleeve body 110. As shown in FIGS. 5B and 5C, the bore surface 110 preferably tapers inwardly toward the central channel axis 120 and toward the distal end 116 of the sleeve body 110.

The proximal and distal ends 114, 116 of the sleeve body 110 can define respective proximal and distal openings 126, 128 of the guide channel 118. The bore surface 124 can be shaped to provide the guide channel 118 with a frusto-conical shape for polyaxial insertion of the drill bit 106 therethrough. Preferably, the frusto-conical shape of the bore surface 124 that defines the guide channel 118 is that of a right circular cone having a central cone axis coincident with the central channel axis 120. The bore surface 124 can thus be oriented at an acute angle A5 from the central channel axis 120, which defines the range of polyaxial angulation of the drill insertion axis 108. The acute angle A5 can be in a range from about 0 degrees to about 10 degrees, and more particularly in a range of about 2.5 degrees to about 7.5 degrees, and more particularly in a range from about 4 degrees to about 6 degrees.

The distal opening 128 is preferably sized to have an opening diameter substantially similar to, but slightly greater than, the diameter of the drill bit 106. In this manner, as shown in FIGS. 5B and 5C, regardless of the selected angulation of the drill insertion axis 108, the drill bit 106 can be caused to advance through the hole 7 (and into underlying bone) at a favorable offset distance O1 for the desired dynamic compression upon subsequent insertion of the screw 8, particularly as the screw shaft 25 advances within the pre-drilled hole in the underlying bone in guiding fashion along the drill insertion axis 108. Thus, for a planned eccentric, nominal screw insertion through the hole 7 to achieve dynamic compression, such as shown in FIGS. 3A and 3B, the physician can employ the guide assembly 102 shown in FIG. 5B in a prior step of pre-drilling into the underlying bone along a nominal drill insertion axis 108 to pre-define, or at least provide guidance for, the planned screw insertion axis 52. Similarly, for a planned eccentric and angulated screw insertion through the hole 7 to achieve dynamic compression, such as shown in FIGS. 4A and 4B, the physician can employ the guide assembly 102 shown in FIG. 5C in a prior step of pre-drilling into the underlying bone along an angulated drill insertion axis 108 to pre-define, or at least provide guidance for, the planned screw insertion axis 52.

The mounting formation 117 is preferably configured to allow the drill guide 104 to be seated within the hole 7 at any rotational orientation (i.e., clocking) about the central hole axis 6. In this manner, the select the position of offset axis 122 (and thus the offset direction O1, and thus also the direction of intended plate translation T1) with respect to the hole 7. The sleeve body 110 can include visual indicia, such as a line, hash mark, arrow, and the like, to provide a visual indication of the offset direction O1. For example, as shown in FIG. 5A, the sleeve body 110 can include a reference arrow 130 pointing in the offset direction O1. The reference arrow 130 can be located on a proximal surface 132 at the proximal end 114 of the sleeve body 110, by way of a non-limiting example. It should be appreciated that the guide channel 118 can have other geometries, including non-polyaxial geometries. In additional embodiments, the bone plating system 100 can include a kit having a plurality of drill guides having guide channels of various shapes and configurations for selective guidance of a drill bit through the hole 7.

Referring now to FIGS. 6A and 6B, the features of the compression hole 7 described above can be incorporated into a combination hole 90, also referred to as a "combi-hole" 90, in which another hole, such as a locking hole 6, such as a VA locking hole 6, intersects the compression hole 7. In such a combi-hole 90, the interior surface 24 further defines a locking surface portion 6a spaced from the compression surfaces 33a-b along a direction 96 perpendicular to axis 94. The locking surface portion 6a extends from the outer plate surface 18 to the bone-facing surface 20 and defines a central locking hole axis 22 spaced from the central compression hole axis 94 along direction 96. The locking surface portion 6a defines at least one locking structure, such as threads 9, configured to engage the threaded head 27 of the VA locking screw 8 in a manner locking the head 27 to the locking surface portion 6a. The at least one locking structure is preferably configured for VA locking with the threaded head 27 of the VA locking screw 8.

The locking hole 6 portion of the combi-hole 90 can be configured according to the embodiments more fully described in the '430 Reference; the '708 Reference; and U.S. application Ser. No. 17/155,218, filed Jan. 22, 2021, in the name of Daniel et al. ("the '218 Reference"), the entire disclosures of each of which are hereby incorporated by reference herein.

The plate body 5 and locking screws 8 described herein can each comprise one or more biocompatible materials. By way of non-limiting examples, the plate body 5 can be formed of a material selected from a group comprising: metal, such as titanium, titanium alloys (e.g., titanium-aluminum-niobium (TAN) alloys, such as Ti-6Al-7Nb, and titanium-aluminum-vanadium (TAV) alloys such as Ti-6Al-4V, titanium molybdenum alloys (Ti—Mo) or any other molybdenum metal alloy, and nickel-titanium alloys, such as nitinol), stainless steel, and cobalt base alloys (e.g., cobalt-chrome alloys); composite materials; polymeric materials; ceramic materials; and/or resorbable materials, including resorbable versions of the foregoing material categories (metals, composites, polymers, ceramics). Also by way of non-limiting examples, the locking screws 8 can be formed of a material selected from a group comprising: metal, such as titanium, titanium alloys (e.g., TAN alloys, TAV alloys, such as Ti-6Al-4V, titanium molybdenum alloys (Ti—Mo) or any other molybdenum metal alloy, and nickel-titanium alloys, such as nitinol), stainless steel, cobalt base alloys (e.g., cobalt-chrome alloys); composite materials; polymeric materials; ceramic materials; and/or resorbable materials, including resorbable versions of the foregoing material categories (metals, composites, polymers, ceramics). Preferably, the material of the locking screws 8 has a hardness that is greater than that of the material of the plate body 5. This parameter contributes to the dynamic compression characteristics and the locking characteristics described throughout the present disclosure. Preferably, the plate body 5 primarily or entirely comprises titanium and the locking screws 8 primarily or entirely comprise TAN. It should be appreciated, however, that other material compositions of the bone plates 4 and/or the screws are within the scope of the present disclosure.

Moreover, surfaces of the plate body 5 and/or the screws can optionally be subjected to one or more processes, such as coating, treating, and/or finishing processes, which can be performed to provide such surfaces, or the underlying subject body material, with certain characteristics, such as to adjust hardness, softness, and/or friction parameters of the body material, as more fully described in the '708 Reference.

It should be appreciated that the various hole 6, 90 parameters described above are provided as exemplary features for adapting the compression holes 6 to achieve selective dynamic compression or locking engagement with the heads 27 of locking screws 8. These parameters can be adjusted as needed without departing from the scope of the present disclosure.

It should also be appreciated that in additional embodiments, the interior surface 24 of any of the compression holes 6 described above can be defined by an insert plate body (e.g., an "insert" or "inlay") that is fitted within an axial aperture or receptacle of the plate body 5. In such embodiments, the bone plate 4 can be provided in a kit that includes a plurality of interchangeable inserts having different compression hole 6 shapes and geometries, such that the physician can select the particular insert having the desired dynamic compression characteristics needed.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed is:

1. A system for bone fixation, comprising:
   a bone plate comprising an outer surface, a bone-facing surface opposite the outer surface, and an interior surface that defines a hole that extends from the outer surface to the bone-facing surface along a central hole axis, wherein the interior surface further defines a compression surface,
     wherein the compression surface is configured to cause translation of the bone plate in a translation direction that is substantially perpendicular to the central hole axis responsive to contact with a threaded portion of an exterior surface of a head of a bone fixation member when the head advances within the hole toward underlying bone along a bone fixation member axis that is offset from the central hole axis at an offset parameter;
   a guide sleeve defining a central sleeve axis, a proximal end, a distal end opposite the proximal end, and a bore surface that defines a guide channel extending from the proximal end to the distal end along a central channel axis that is offset from the central sleeve axis along an offset axis oriented along a second direction that is perpendicular to the central sleeve axis, wherein the distal end of the guide sleeve defines a mounting formation configured to seat against the interior surface within the hole such that the central sleeve axis is substantially parallel to the central hole axis, wherein the bore surface tapers toward the central channel axis and toward the distal end such that the bore surface is configured to provide guided polyaxial insertion of a drill through the hole toward the underlying bone along a selective trajectory axis that defines the offset parameter, wherein the mounting formation of the guide sleeve is configured to seat against the interior surface of the bone plate such that the offset axis is oriented at a selective angular position from 0 degrees at least to 360 degrees about the central hole axis while the central sleeve axis is substantially parallel to the central hole axis.

2. The system of claim 1, wherein the compression surface tapers inwardly toward the central hole axis and toward the bone-facing surface, and the interior surface defines a countersink that extends from the outer surface toward the compression surface.

3. The system of claim 2, wherein the interior surface further defines a landing between the countersink and the compression surface, the landing extending from a lower perimeter of the countersink toward the central hole axis.

4. The system of claim 3, wherein the mounting formation of the sleeve comprises a first portion and a second portion, wherein, when the mounting formation is fully seated within the hole, the first portion is configured to abut the landing and the second portion is configured to abut the compression surface.

5. The system of claim 1, wherein the hole is a combination hole, such that the interior surface further defines a locking surface portion spaced from the compression surface, wherein the central hole axis is a central compression hole axis, the locking surface portion extends from the outer surface toward the bone-facing surface and defines a central locking hole axis spaced from the central compression hole axis along a direction perpendicular to the central hole axis, and the locking surface portion defines at least one variable-angle locking structure configured to engage the threaded portion of the head in a manner locking the head to the bone plate.

6. A system for bone fixation, comprising:
a bone plate comprising an outer surface, a bone-facing surface opposite the outer surface, and an interior surface that defines a hole that extends from the outer surface to the bone-facing surface along a central hole axis, wherein the interior surface further defines:
a first compression surface that tapers inwardly toward the central hole axis and toward the bone-facing surface;
a countersink that extends from the outer surface toward the first compression surface, wherein the first compression surface extends between the countersink and the bone-facing surface;
a landing between the countersink and the first compression surface, the landing extending from a lower perimeter of the countersink toward the central hole axis; and
at least one additional compression surface extending from the landing to the first compression surface;
a bone fixation member having a head and a shaft that extends from the head along a central fixation member axis, wherein the head has an exterior surface that defines a threaded head portion, wherein the threaded head portion is configured for variable angle locking with a complimentary variable angle plate locking structure, wherein the first compression surface and the threaded head portion are cooperatively configured to translate the bone plate in a translation direction that is substantially perpendicular to the central hole axis responsive to the threaded head portion contacting the first compression surface when the bone fixation member axis is offset from the central hole axis at an offset parameter as the head advances within the hole toward underlying bone, and wherein the at least one additional compression surface is configured to contact the exterior surface of the head in a manner causing at least a portion of the translation.

7. The system of claim 6, wherein the offset parameter is one or more of an offset distance measured from the central hole axis to the central fixation member axis along a direction perpendicular to the central hole axis and an offset angle measured between the central hole axis and the central fixation member axis.

8. The system of claim 6, wherein the first compression surface defines a minimum inner diameter measured along a direction perpendicular to the central hole axis, and the threaded head portion defines a head diameter that is greater than the minimum inner diameter, such that the central fixation member axis is colinear with or at least substantially intersects the central hole axis when the head is fully seated against the first compression surface at a conclusion of the translation.

9. The system of claim 6, wherein the hole is a combination hole, such that the interior surface further defines a locking surface portion spaced from the first compression surface, wherein the central hole axis is a central compression hole axis, the locking surface portion extends from the outer surface toward the bone-facing surface and defines a central locking hole axis spaced from the central compression hole axis along a direction perpendicular to the central hole axis, and the locking surface portion defines at least one variable-angle locking structure configured to engage the threaded head portion in a manner locking the head to the bone plate.

10. The system of claim 6, further comprising a guide sleeve insertable within the hole, the guide sleeve defining a central sleeve axis, a proximal end, a distal end opposite the proximal end, and a bore surface that defines a guide channel extending from the proximal end to the distal end along a central channel axis that is offset from the central sleeve axis along an offset axis oriented along a second direction that is perpendicular to the central sleeve axis, wherein the distal end of the guide sleeve defines a mounting formation configured to seat against the interior surface within the hole such that the central sleeve axis is substantially parallel to the central hole axis, wherein the bore surface tapers toward the central channel axis and toward the distal end such that the bore surface is configured to provide guided poly axial insertion of a drill through the hole toward the underlying bone along a selective drill insertion axis that defines the offset parameter.

11. The system of claim 10, wherein the mounting formation is configured to seat against the interior surface such that the offset axis is oriented at a selective angular position from 0 degrees at least to 360 degrees about the central hole axis while the central sleeve axis is substantially parallel to the central hole axis.

12. The system of claim 6, wherein the first compression surface defines one or more threads configured to engage threads of the threaded head portion of the bone fixation member.

13. A method of bone fixation, comprising:

inserting a shaft of a bone fixation member through a hole in a bone plate along an insertion axis and into underlying bone, wherein the bone plate comprises an outer surface, a bone-facing surface opposite the outer surface, and an interior surface that defines the hole, wherein the hole extends along a central hole axis, and the insertion axis is offset from the central hole axis at an offset parameter, contacting a threaded portion of an exterior surface of a head of the bone fixation member against a first compression surface and a second compression surface within the hole, wherein each of the first and second compression surfaces is defined by the interior surface and taper inwardly toward the central hole axis and toward the bone-facing surface, wherein the interior surface further defines:

a countersink that extends from the outer surface toward the first compression surface, wherein the first compression surface extends between the countersink and the bone-facing surface; and a landing between the countersink and the first compression surface, wherein the landing extends from a lower perimeter of the countersink toward the central hole axis, and the second compression surface extends from the landing to the first compression surface; and driving the bone fixation member, during the contacting step, toward the underlying bone along the insertion axis in a manner translating the bone plate in a translation direction that is substantially perpendicular to the central hole axis.

14. The method of claim 13, wherein the offset parameter is one or more of an offset distance measured from the central hole axis to the insertion axis along a direction perpendicular to the central hole axis and an offset angle measured between the central hole axis and the insertion axis.

15. The method of claim, 13, further comprising, prior to the inserting step, advancing a drill bit through the hole and pre-drilling into the underlying bone along the insertion axis.

16. The method of claim 15, further comprising:

prior to advancing the drill bit through the hole, seating a distal end of a drill guide within the hole, wherein the step of advancing the drill bit through the hole comprises advancing the drill bit through a guide channel defined by the drill guide, wherein the guide channel extends from a proximal end to a distal end of the drill guide along a central channel axis that is offset from the central hole axis along an offset axis oriented along a second direction that is perpendicular to the central hole axis when the distal end of the drill guide is seated within the hole, wherein the guide channel is defined by a bore surface that tapers toward the central channel axis and toward the distal end such that the bore surface is configured to provide guided poly axial insertion of the drill bit through the hole toward the underlying bone.

* * * * *